(12) United States Patent
Nilsson et al.

(10) Patent No.: US 9,895,504 B2
(45) Date of Patent: Feb. 20, 2018

(54) SYSTEM AND DEVICE FOR NEONATAL RESUSCITATION AND INITIAL RESPIRATORY SUPPORT

(75) Inventors: Kjell Nilsson, Östersund (SE); Thomas Drevhammar, Östersund (SE)

(73) Assignee: Neores AB, Ostersund (SE)

( * ) Notice: Subject to any disclaimer, the term of this patent is extended or adjusted under 35 U.S.C. 154(b) by 216 days.

(21) Appl. No.: 13/977,283

(22) PCT Filed: Feb. 8, 2012

(86) PCT No.: PCT/SE2012/050119
§ 371 (c)(1),
(2), (4) Date: Aug. 26, 2013

(87) PCT Pub. No.: WO2012/108826
PCT Pub. Date: Aug. 16, 2012

(65) Prior Publication Data
US 2013/0327332 A1      Dec. 12, 2013

Related U.S. Application Data (60) Provisional application No. 61/440,409, filed on Feb. 8, 2011.

(30) Foreign Application Priority Data

Feb. 8, 2011    (SE) ...................... 1150092

(51) Int. Cl.
*A61M 16/00*     (2006.01)
*A61M 16/12*     (2006.01)
(Continued)

(52) U.S. Cl.
CPC .... *A61M 16/0057* (2013.01); *A61M 16/0875* (2013.01); *A61M 16/1015* (2014.02);
(Continued)

(58) Field of Classification Search
CPC ............ A61M 16/057; A61M 16/1015; A61M 16/209; A61M 16/208; A61M 16/0875;
(Continued)

(56) References Cited

U.S. PATENT DOCUMENTS 4,227,523 A * 10/1980 Warnow et al. .......... 128/204.24
4,502,481 A *  3/1985 Christian .............. A61M 16/00
                                                       128/205.24

(Continued)

FOREIGN PATENT DOCUMENTS

CN    101918062 A    12/2010
GB      2465358 A     5/2010
(Continued)

OTHER PUBLICATIONS

Chinese Office Action dated Jan. 12, 2015 issued in corresponding Chinese Application No. 201280006338.7 (with English translation).

(Continued)

*Primary Examiner* — Peter S Vasat
*Assistant Examiner* — Margaret Luarca
(74) *Attorney, Agent, or Firm* — Harness, Dickey & Pierce, P.L.C.

(57) ABSTRACT

The present invention relates to a device and a system for positive pressure ventilation and continuous positive airway pressure (CPAP) treatment for neonatal resuscitation and initial respiratory support. The device and system are designed and tested for preterm and term neonatal use. The device is easy to use and allows rapid switch between PPV and CPAP without change of equipment and significantly reduces the imposed work of breathing for a breathing child treated with CPAP.

12 Claims, 6 Drawing Sheets

(51) Int. Cl.
*A61M 16/20* (2006.01)
*A61M 16/10* (2006.01)
*A61M 16/08* (2006.01)

(52) U.S. Cl.
CPC .......... *A61M 16/12* (2013.01); *A61M 16/208* (2013.01); *A61M 16/209* (2014.02); *A61M 16/0816* (2013.01); *A61M 2016/003* (2013.01); *A61M 2016/0027* (2013.01); *A61M 2202/0208* (2013.01); *A61M 2240/00* (2013.01)

(58) Field of Classification Search
CPC .......... A61M 16/12; A61M 2202/0208; A61M 16/0816; A61M 2016/0027; A61M 2240/00; A61M 16/0883; A61M 16/206; A61M 16/207; A62B 9/02; A62B 9/027
USPC .................. 128/205.24, 202.27, 204.18, 912
See application file for complete search history.

(56) References Cited

U.S. PATENT DOCUMENTS

| | | | |
|---|---|---|---|
| 5,116,088 A * | 5/1992 | Bird | ............................ 285/319 |
| 5,193,532 A * | 3/1993 | Moa et al. | ................ 128/204.25 |
| 5,862,802 A * | 1/1999 | Bird | ...................... A61M 16/00 |
| | | | 128/204.18 |
| 6,269,811 B1 * | 8/2001 | Duff | ...................... A61M 16/12 |
| | | | 128/204.18 |
| 6,612,304 B1 * | 9/2003 | Cise et al. | ................. 128/200.26 |
| 7,578,294 B2 | 8/2009 | Pierro et al. | |
| 7,640,934 B2 | 1/2010 | Zollinger et al. | |
| 7,987,850 B2 | 8/2011 | Zollinger et al. | |
| 2007/0125379 A1 | 6/2007 | Pierro et al. | |
| 2007/0125387 A1 | 6/2007 | Zollinger et al. | |
| 2009/0301495 A1 | 12/2009 | Pierro et al. | |
| 2010/0108073 A1 | 5/2010 | Zollinger et al. | |
| 2010/0163046 A1 | 7/2010 | Fisher et al. | |
| 2010/0319691 A1 | 12/2010 | Lurie et al. | |
| 2011/0011395 A1 * | 1/2011 | Mazela et al. | ............ 128/202.13 |
| 2013/0087146 A1 * | 4/2013 | Callaghan et al. | ....... 128/204.21 |

FOREIGN PATENT DOCUMENTS

| | | | | |
|---|---|---|---|---|
| WO | WO1999/08738 | * | 2/1999 | ............ A61M 16/00 |
| WO | WO-2009/078805 A1 | | 6/2009 | |
| WO | WO 2009078805 A1 | * | 6/2009 | ............ A61M 16/06 |

OTHER PUBLICATIONS

International Search Report PCT/ISA/210 for International Application No. PCT/SE2012/050119 dated May 10, 2012.

* cited by examiner

SYSTEM AND DEVICE FOR NEONATAL RESUSCITATION AND INITIAL RESPIRATORY SUPPORT

This application is the national phase under 35 U.S.C. § 371 of PCT International Application No. PCT/SE2012/050119 which has an International filing date of Feb. 8, 2012, which designated Sweden and which claims priority to Swedish patent application number SE 1150092-3 filed Feb. 8, 2011 and U.S. provisional patent application No. 61/440,409 filed Feb. 8, 2011.

FIELD OF THE INVENTION

The present invention relates to a device and a system for positive pressure ventilation (PPV) and continuous positive airway pressure (CPAP) treatment for neonatal resuscitation and initial respiratory support. The device and system is designed and tested for preterm and term neonatal use.

BACKGROUND OF THE INVENTION

Today there are primarily two systems for positive pressure ventilation in use, i.e. the simple T-piece or a bag. Both use a mask as an interface to the child but can also be used via an ET-tube. The two systems are easy to handle, uncomplicated and inexpensive and have been in use for many decades.

The T-piece systems are able to provide positive pressure ventilation as well as CPAP for a breathing infant but the bag systems are unable to provide CPAP for the breathing infant.

In neonatal resuscitation there is a need for both ventilation (PPV) of the non-breathing child and support by CPAP for the spontaneously breathing child. The need for both types of support is common and changes over time during the resuscitation period.

An example of a T-piece system is disclosed in U.S. Pat. No. 4,502,481, where an inspiratory tube provides a fresh gas flow from a fresh gas source to the patient mask, and an expiratory tube outlets used gas from the patient mask via a two-way exhaust valve. In the CPAP mode the T-piece system feeds pressurised fresh gas to the patient mask and outlets used gas and excessive fresh gas through a first path of the exhaust valve which is set at a relatively low opening pressure. In the PPV mode, this path is manually intermittently occluded. When occluded the pressure at the patient mask rises and fresh gas is forced into the patient. When not occluded the patient exhales. If reaching a maximum allowed pressure before the occlusion is removed, the second path of the exhaust valve opens to avoid patient injury.

Thus, the T-piece systems can also provide both PPV and CPAP. However, these systems expose the neonate to a higher imposed work of breathing than most of the specialised CPAP systems. This may lead to extended period of PPV. This could be overcome by switching between two systems—one for PPV and a specialised system for CPAP but this is unpractical in the resuscitation period. Furthermore, specialised CPAP systems are comparatively expensive.

Therefore there is a need within the technical field of PPV/CPAP treatment for neonatal resuscitation to overcome the problems that exist today. There is a need to achieve an easy switch between PPV and CPAP for respiratory support without change of equipment and to provide a low imposed work of breathing for the breathing child treated with CPAP.

SUMMARY OF THE INVENTION

It is an object of the present invention to provide a device for PPV and CPAP treatment that alleviates the above mentioned problems.

The object is achieved by a device for PPV and CPAP treatment according to the present invention as defined in claim 1.

Thus, in accordance with an aspect of the present invention, there is provided a device for positive pressure ventilation and continuous positive airway pressure treatment for neonatal resuscitation comprising:
  a first fresh gas flow tube, arranged to provide a first fresh gas flow;
  a variable flow continuous positive airway pressure generator comprising first, second and third connection portions, wherein the first fresh gas flow tube is connected with the first connection portion, wherein the generated continuous positive airway pressure level is adjusted by varying the fresh gas flow to the variable flow continuous positive airway pressure generator;
  a connector connected with the second connection portion of the variable flow continuous positive airway pressure generator, wherein the connector is arranged to be connected with an infant interface; and
  a pressure release valve, arranged to prevent an excessive positive pressure in a positive pressure ventilation mode;
  wherein the third connection portion embodies an outlet, the device further comprising:
  a second fresh gas flow tube, arranged to provide a second fresh gas flow, which is added to the first fresh gas flow in the positive pressure ventilation mode.

The device is designed and tested for preterm and term neonatal use. It is not intended for adult use. The device is easy to use and allows rapid switch between PPV and CPAP without change of equipment. A safe and quick switch between these types of respiratory support will improve care for an unstable child and lead to higher quality in resuscitation with reduced mortality and morbidity. Due to the second fresh gas tube, the inspiratory flow in the PPV mode is increased, such that when the outlet is occluded the second flow adds to the first flow and rapidly increases the pressure and generates an inspiration. Furthermore, the device significantly reduces the imposed work of breathing for a breathing child treated with CPAP, inter alia due to the absence of mechanical valves at the outlet. A reduction of imposed work of breathing should lead to higher quality in resuscitation with reduced mortality and morbidity. It should also reduce the need for PPV.

For purposes of this invention, the words "infant" and "child" are intended to encompass a patient such as a newborn, a neonatal child which is in need of neonatal resuscitation and initial respiratory support.

For purposes of this invention, the wording "fresh gas flow" is compressed air, compressed oxygen or a mixture of these that flows through the system and its parts and the wording "fresh gas flow tube" is wherein the fresh gas flows.

For purposes of this invention, the wording "bypass gas flow" will be used as a synonym to "second fresh gas flow", since the second fresh gas flow does not drive the variable flow CPAP generator as does the first fresh gas flow, i.e. in a sense the second fresh gas flow bypasses the variable flow CPAP generator. The wording "fresh gas flow" is compressed air, compressed oxygen or a mixture of these that flows through the device or system and its parts, and the wording "tube" is wherein the fresh gas flows.

For purposes of this invention, the wording "variable flow CPAP generator" is a device intended to encompass any continuous positive airway pressure device were the CPAP level is adjusted by varying the fresh gas flow.

For purposes of this invention, the wording "imposed work of breathing" is the additional work required to breathe through a device and is an established way of measuring the pressure stability of a system. Imposed work of breathing is obtained by calculating the area within a pressure-volume loop for one breath.

For purposes of this invention, the word "infant interface" is intended to encompass any interface that is suitable for connecting to an infant or child, such as a pair of nasal prongs, a mask or any other suitable device.

In accordance with an embodiment of the device, the second fresh gas flow tube is connected with one of the connector and the third connection portion. These are two alternative ways of arranging the second fresh gas flow tube in order to achieve the advantages set forth above.

In accordance with an embodiment of the device, the pressure release valve is connected with one of the second fresh gas flow tube, the connector, and the third connection portion. These are three alternative ways of arranging the pressure release valve, where the main aim is to arrange it in a position where the pressure of interest is measurable in a reliable way.

In accordance with an embodiment of the device, the second fresh gas flow tube is connected through a wall of the third connection portion, wherein the third connection portion comprises an open end defining the outlet. This embodiment emphasizes the absence of mechanical valves, such as the overpressure valve 13 of the prior art device disclosed in U.S. Pat. No. 4,502,481, as described above, thereby minimising the imposed breathing work.

In accordance with an embodiment of the device, the first fresh gas flow in the device to the variable flow CPAP generator is in the range of 3-12 liters per minute and the second fresh gas flow is in the range of 3-12 liters per minute.

In accordance with an embodiment of the device, it further comprises a pressure measuring device. Thereby, it is possible to easily monitor the operation of the device and make desirable adjustments of for instance the first fresh gas flow. Preferably, the pressure measuring device is connected with the connector or with the second fresh gas flow tube in case the second fresh gas flow tube, in turn, is connected with the connector.

The different embodiments of the device can be summarized as a device comprising a first fresh gas flow tube connected to a variable flow CPAP generator, a connector connected to the variable flow CPAP generator, a bypass flow tube connected to an outlet of the variable flow CPAP generator or to the connector, a pressure release valve connected to the outlet of the variable flow CPAP generator or to the connector or to the bypass flow tube, and a pressure measuring device connected to the connector or to the bypass flow tube if the bypass flow tube is connected to the connector.

According to another aspect of the present invention, there is provided a system for positive pressure ventilation and continuous positive airway pressure treatment for neonatal resuscitation comprising a device as described above, and a fresh gas connection unit, connected with the first and second fresh gas flow tubes, and connectable to at least one fresh gas source. Thus, the system includes the connection unit which is connected to at least one fresh gas source. In case of a single fresh gas source, the connection unit is a device which splits the received fresh gas flow in two flows, which are conducted into the first fresh gas flow tube and into the second fresh gas flow tube, respectively. Multiple fresh gas sources may be used to provide either the same fresh gas in two different paths, or different fresh gases, which are mixed in the fresh gas connection unit.

In accordance with an embodiment of the system, it is arranged such that when the open end outlet (8) of the outlet (4) of the variable flow CPAP generator is occluded the pressure will increase from the variable CPAP generator until the opening pressure of the release valve (6) is reached, the increase in pressure results to an inspiratory flow, the pressure in the system will remain at the set positive pressure ventilation pressure until the outflow occlusion is removed, when the occluded outflow is opened the pressure will return to the set CPAP level and this reduction in pressure will lead to an expiratory flow.

In accordance with an embodiment of the system, it is arranged such that during spontaneous breathing, the infant flow and the fresh gas flow leaves the breathing system over the variable flow CPAP generator 3 keeping the positive pressure within the airway stable, by varying the fraction of flow that generates the CPAP pressure the CPAP pressure in the airway can be adjusted as needed.

The device as disclosed above can be used in positive pressure ventilation and continuous positive airway pressure treatment for neonatal resuscitation.

The system as disclosed above can be used for positive pressure ventilation and continuous positive airway pressure treatment for neonatal resuscitation.

These and other aspects, and advantages of the invention will be apparent from and elucidated with reference to the embodiments described hereinafter.

BRIEF DESCRIPTION OF THE DRAWINGS

The invention will now be described in more detail and with reference to the appended drawings. The drawings are included to provide a further understanding of the present invention and are incorporated in and are a part of this specification. Other embodiments of the present invention, and many of the intended advantages of the present invention, will be readily appreciated as they become better understood by reference to the following detailed description. The elements of the drawings are not necessarily to scale relative to each other. The same reference numerals designate corresponding similar parts.

DESCRIPTION OF PREFERRED EMBODIMENTS

For resuscitation and stabilisation of newborn infants two types of mechanical respiratory support are common depending on whether the infant is breathing or not. Positive pressure ventilation is used for the non-breathing infant and continuous positive airway pressure for the breathing infant. An infant that is not breathing after birth should be ventilated. This can be accomplished with PPV using e.g. a face mask, or an endotracheal tube. In the majority of cases a mask is used. If the infant starts to breath or was breathing after birth, support of ventilation using CPAP is the recommended treatment for several conditions. After return of spontaneous breathing some infants will still need PPV intermittently as they stop breathing. This is especially common when treating premature neonates.

The advantages with the present invention is that it allows rapid and easy switch, without change of equipment, between PPV and CPAP treatment in combination with a significant reduction in imposed work of breathing compared to available devices. Today in order to provide CPAP with low imposed work of breathing a device that is unable to provide PPV has to be used. Should the infant require ventilation a switch to another system able to provide positive pressure ventilation will be needed such as a bag or T-piece system.

There are examples of different embodiments of the present invention. Common for the embodiments described herein is that they comprise a first fresh gas flow tube 1, a second fresh gas flow tube 2, a variable CPAP generator 3, a connector 9, and a pressure release valve 6. Some embodiments additionally comprise a pressure measuring device 7. Furthermore, the variable flow CPAP generator 3 comprises a first connection portion, a second connection portion, and a third connection portion 4. In all embodiments, the first fresh gas flow tube 1 is connected with the first connection portion of the variable flow CPAP generator 3; the connector 9 is connected with the second connection portion; and the third connection portion 4 embodies an outlet 4 of the variable flow CPAP generator 3. The outlet 4 typically is tubular, and is arranged as a protruding tube ending at a free open end. There are no mechanical valves as in the prior art described above. The connector 9 is typically realised as a tube having a first end connected with the second connection portion, and a second end is connectable with any infant interface 5, examples of which have been given above.

The second fresh gas flow tube will also be called bypass flow tube, since in most embodiments and operation modes the second fresh gas flow will bypass the variable CPAP generator 3. The bypass flow tube 2, the pressure measuring device 7 and the pressure release valve 6 can be arranged in several different positions, see FIGS. 1-4. The pressure measuring device 7 can be omitted in any embodiment if there is no interest in measuring the pressure.

Figure 1:
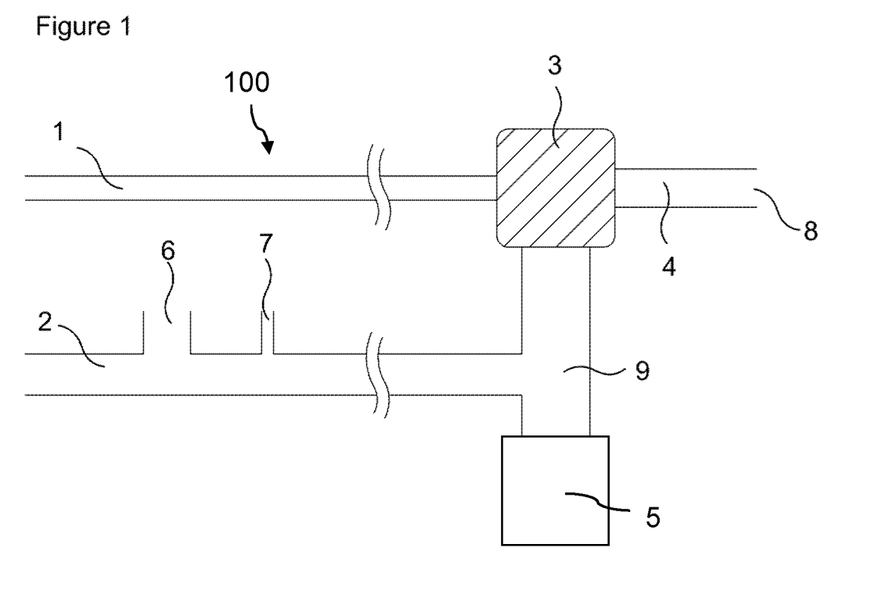
FIG. 1 is a schematic illustration of an embodiment of the device according to the present invention.

As disclosed in FIG. 1, according to a first embodiment of the device 100, the bypass flow tube 2 is connected to the connector 9, i.e. through the wall of the connector 9, between the variable flow CPAP generator 3 and infant interface 5. This connection of the bypass flow tube 2 is preferred. The pressure release valve 6 and the pressure measuring device 7 are connected to the bypass flow tube 2.

Figure 2:
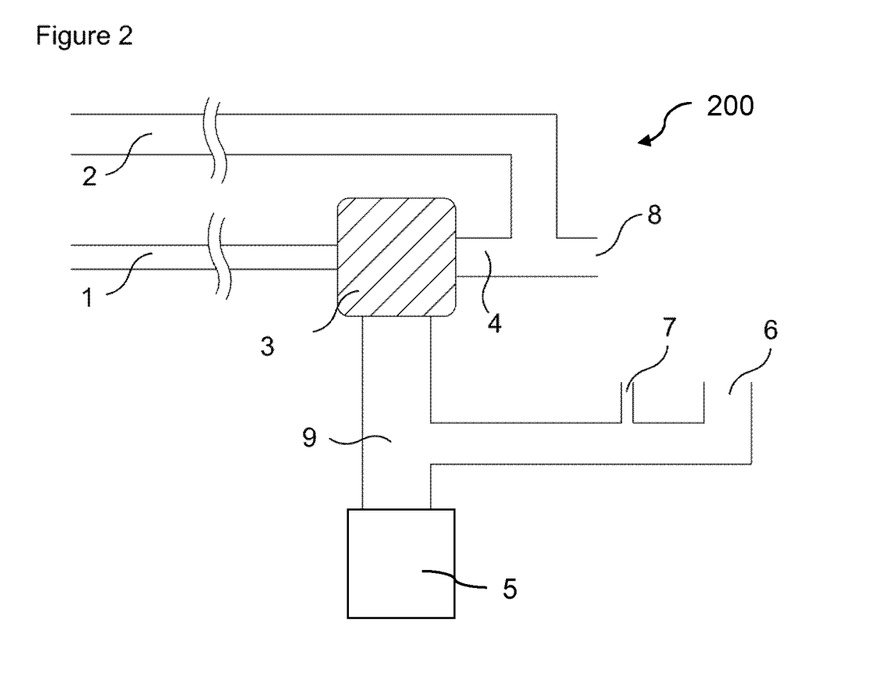
FIGS. 2-4 are schematic illustrations of further embodiments of the device.

As disclosed in FIG. 2, according to a second embodiment of the device 200, the bypass flow tube 2 is connected to the outlet 4, i.e. through the wall of the outlet 4, of the variable flow CPAP generator 3. The pressure release valve 6 and the pressure measuring device 7 are connected to the connector 9 between the infant interface 5 and the variable flow CPAP generator 3.

Figure 3:
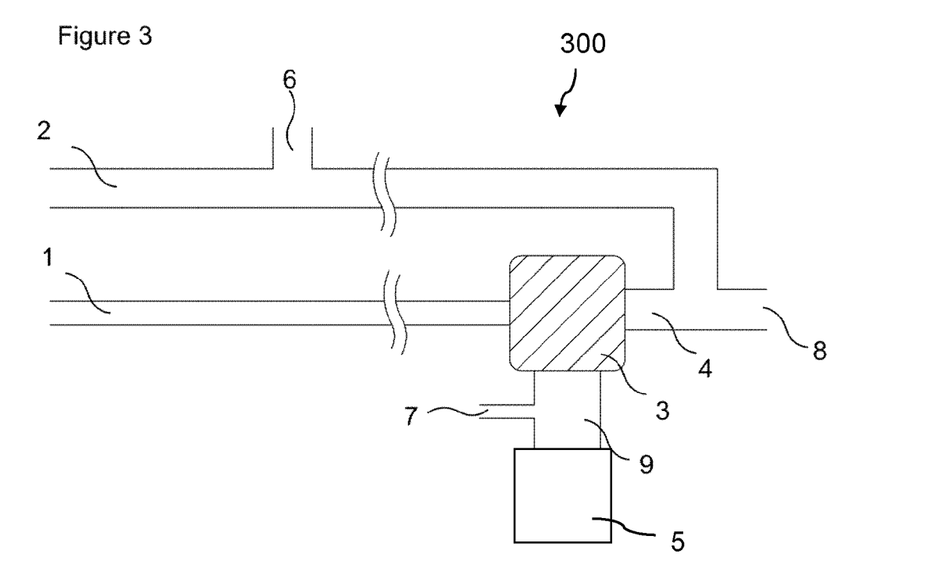

As disclosed in FIG. 3, according to a third embodiment of the device 300, the bypass flow tube 2 is connected to the outlet 4 of the variable flow CPAP generator 3. The pressure release valve 6 is connected on the bypass flow tube 2. The pressure measuring device 7 is connected to the connector 9 between the infant interface 5 and the variable flow CPAP generator 3.

Figure 4:
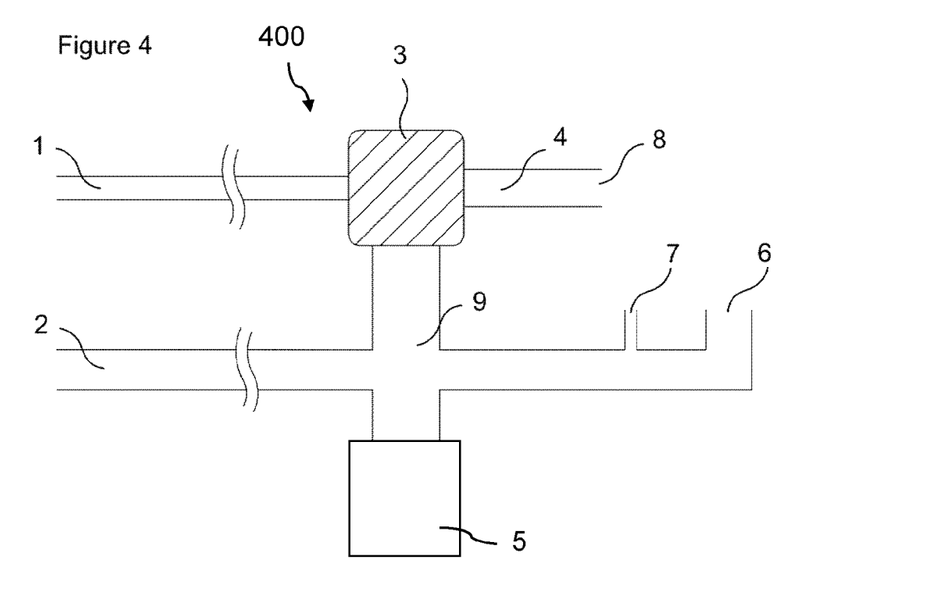
Figure 5A:
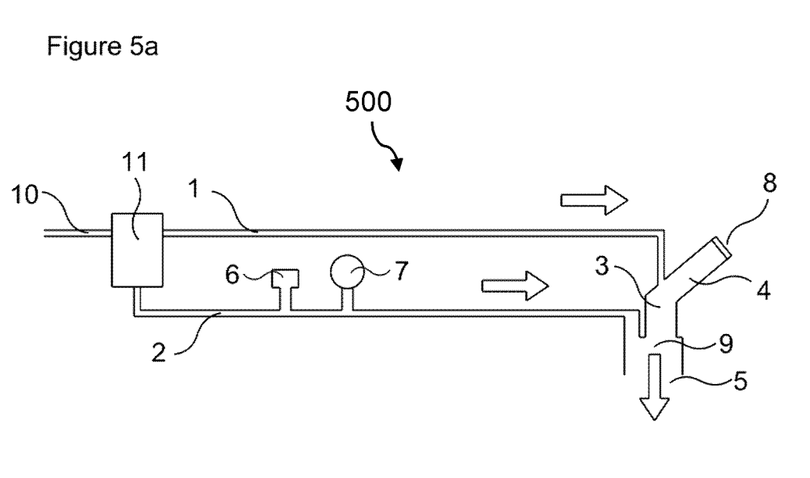
FIGS. 5a-5c schematically illustrate flows in an embodiment of the system according to the present invention, during positive pressure ventilation.
Figure 5B:
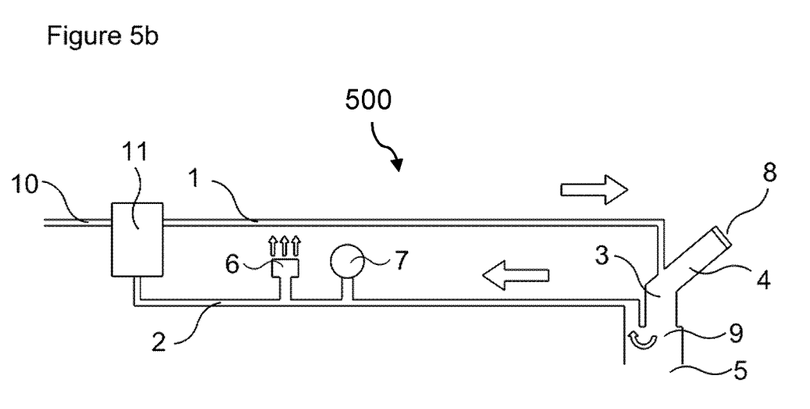
Figure 5C:
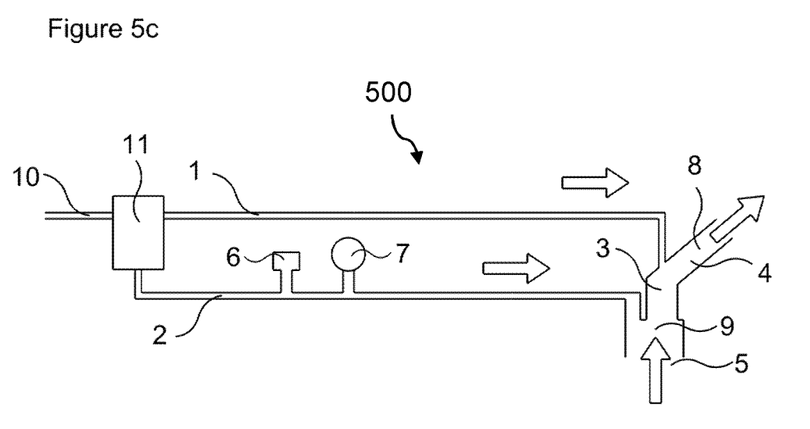

As disclosed in FIG. 4, according to a fourth embodiment of the device 400, the bypass flow tube 2 is connected to the connector 9 between the variable flow CPAP generator 3 and the infant interface 5. The pressure release valve 6 and the pressure measuring device 7 are connected to the connector 9 between the infant interface 5 and the variable flow CPAP generator 3.

A first embodiment of the system 500, as disclosed in FIGS. 5a-5c and 6, comprises the first embodiment of the device 100. The system further comprises a fresh gas connection unit 11, which is connected to a fresh gas flow 10 originating from a fresh gas source (not shown). The fresh gas connection unit 11 is a shunt, which splits the fresh gas flow 10 into the first and second fresh gas flows fed through the first and second fresh gas flow tubes 1, 2, respectively, and adjusts the level of CPAP.

Figure 8:
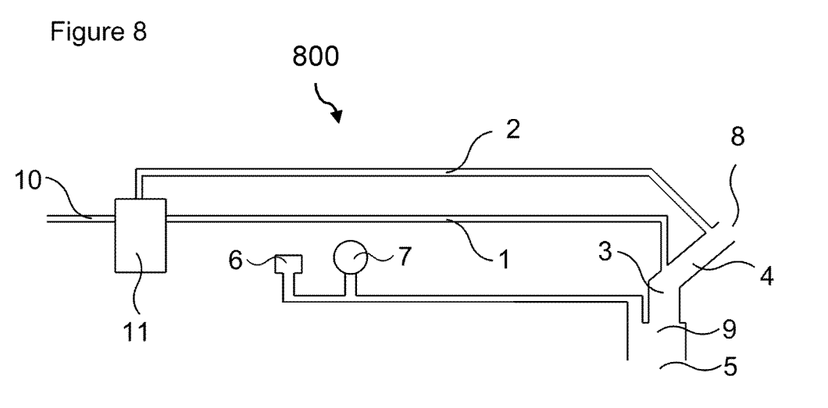
FIG. 8 schematically illustrates another embodiment of the system.

A second embodiment of the system 800, as disclosed in FIG. 8, comprises the second embodiment of the device 200, and a fresh gas connection unit 11.

The system is operated as follows. Reference will be made to the first embodiment of the system 500, but the second embodiment 800 has a corresponding operation. Oxygen concentration and fresh gas flow are adjusted by a standard blender and a flow meter. The fresh gas flow could be varied and typically between 10-15 liters (l) per minute. A fresh gas flow in this range should prevent rebreathing, provide flow to achieve an adequate inspiration flow, volume and time, and provide some allowance for leak in the infant interface 5.

The fresh gas flow 10 can be supplied from two different gas sources or from the same gas source. If one gas source is used then the fresh gas flow is divided into two fractions. The fresh gas flow can be divided using a shunt valve or double rotameter or any other device capable of dividing a gas flow. One part of the fresh gas flow, i.e. the first fresh gas flow, is used to drive the variable flow CPAP generator 3 and the other part of the fresh gas flow, i.e. the second fresh gas flow or bypass flow, is used to supply adequate flow for positive pressure ventilation by bypassing the variable flow CPAP generator 3. The bypass flow is connected in such a way that it adds to inspiratory patient flow when the device is occluded during positive pressure ventilation. The first fresh gas flow to the variable CPAP generator 3 is always adjustable. The bypass flow can be varied or fixed. A typical value of the first fresh gas flow to the variable flow CPAP generator is 3-12 liters per minute and the bypass flow is 3-12 liters per minute. The sum of the first fresh gas flow and the bypass flow will typically be between 10-15 l per minute. To provide high CPAP the flow driving the variable flow CPAP generator can be increased further until the bypass flow is zero. This would generate a CPAP that is higher than normally used.

The outlet 4 of the variable flow CPAP generator 3 has an open end outlet 8. If the open end outlet 8 is occluded, see FIGS. 5a and 5b, the pressure delivered to the infant will increase from the pressure set by the variable CPAP generator 3 until the opening pressure of the release valve 6 is reached. A typical value for the pressure release valve 6 to open is around 20-30 cm $H_2O$. The increase in pressure results in an inspiratory flow. The pressure in the system 500 will remain at the set positive pressure ventilation pressure until the outlet occlusion is removed. When the occluded open end outlet 8 is opened, see FIG. 5c, the pressure delivered to the patient will return to the set CPAP level and this reduction in pressure will lead to an expiratory flow.

Figure 6:
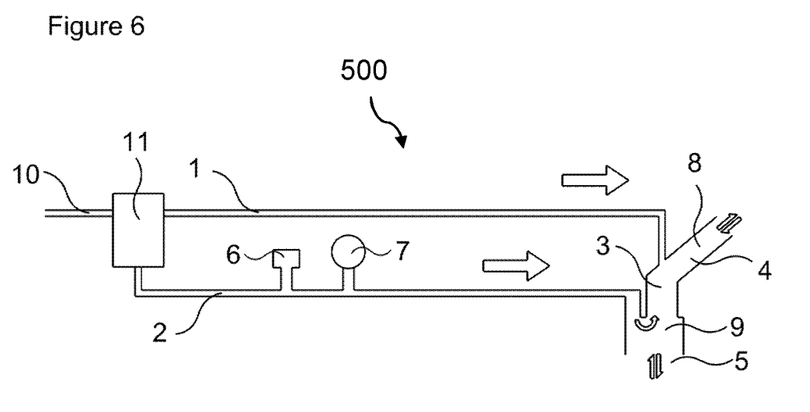
FIG. 6 schematically illustrates flows in the system shown in FIGS. 5a-5c during spontaneous ventilation.

During spontaneous breathing the infant flow and the fresh gas flow leaves the breathing system over the variable flow CPAP generator 3, see FIG. 6. This keeps the positive pressure within the airway stable. By varying the fraction of flow, i.e. the first fresh gas flow, that generates the CPAP pressure, the CPAP pressure in the airway can be adjusted as needed. The first fresh gas flow drives the variable flow CPAP generator 3 and the bypass flow bypasses the variable flow CPAP generator 3.

The connector 9 between variable flow CPAP generator 3 and infant interface 5 can be designed in any suitable form.

The system could have a backup system for malfunctioning of the pressure release valve 6. This could either be an alarm, a second release valve or a system that cuts the fresh gas flow.

The infant interface 5 can assume a variety of designs suitable for establishing a connection to the infant nasal airways, not shown. Thus, the infant interface 5 can include an opposing pair of nasal prongs, a mask or any other suitable devices.

The pressure measuring device 7 should be positioned as close to the infant as possible to provide accurate recording of the pressure of the gas delivered to the infant. The accuracy will depend on the flow resistance of the infant interface 5 and a low resistance interface should be used if possible. The first embodiment of the device 100 could be regarded as beneficial since there will be less tubes needed in the system.

Figure 7:
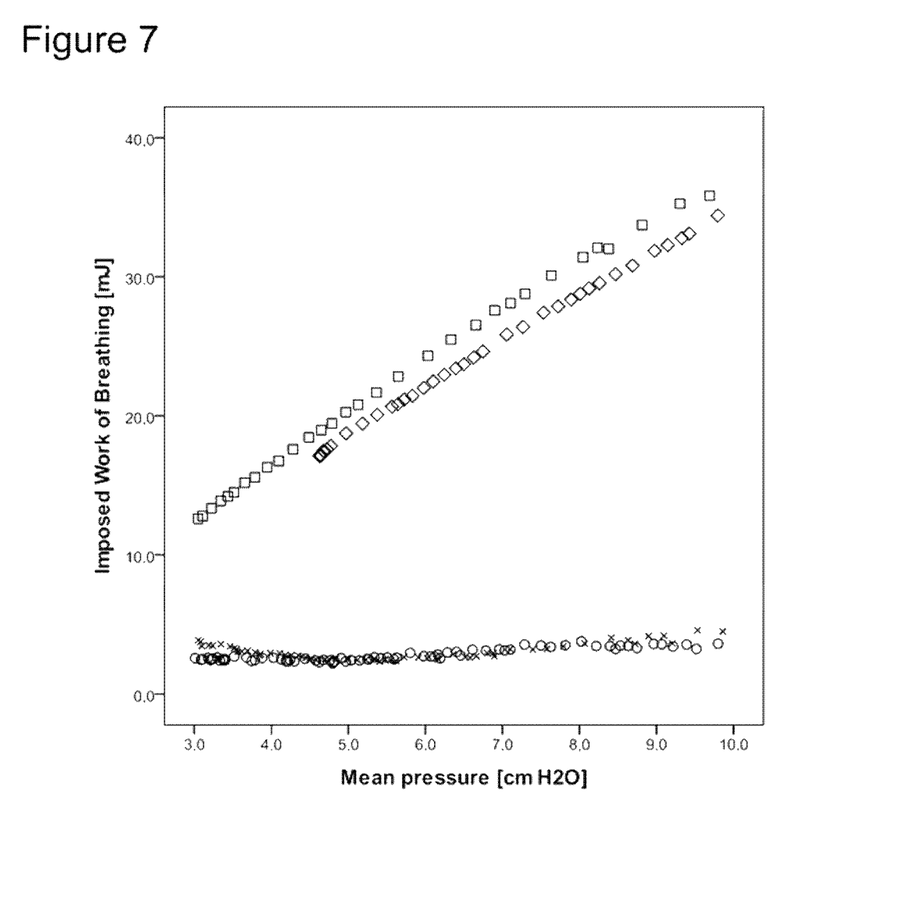
FIG. 7 is a scatter plot showing the imposed work of breathing at different levels of CPAP, the mean pressure, for different systems determined by simulated breathing in a mechanical lung model.

A comparison of the reduction in imposed work of breathing at different levels of CPAP is made between two embodiments of the present invention and two other systems, and the results are disclosed in FIG. 7. The mean pressure is the average pressure for one breath and is very similar to CPAP. Imposed work of breathing is the additional work required to breathe through a device and is an established way of measuring the pressure stability of a system. Imposed work of breathing is obtained by calculating the area within a pressure-volume loop for one breath. In FIG. 7 the GE Healthcare T-piece is represented by diamonds, Neopuff™ from Fisher & Paykel is represented by squares, prototype A is represented by crosses and prototype B is represented by circles. Prototype A uses the device described in FIG. 1 and prototype B uses the device described in FIG. 3.

Notably, the device, in accordance with principles of the present invention is useful with a wide variety of infant interface configurations that may or may not incorporate some or all of the features described above with respect to the infant interface. Thus, the infant interface is in no way limiting. The infant interface is connected to the open end of the connector 9, i.e. the end which is not connected to the variable flow CPAP generator 3.

Notably, the device, in accordance with principles of the present invention is useful with a wide variety of variable flow CPAP generators that may or may not incorporate some or all of the features described above with respect to the variable flow CPAP generators. Thus, the model of the variable flow CPAP generator is in no way limiting.

Notably, the device, in accordance with principles of the present invention is useful with a wide variety of pressure release valves or similar devices that achieves the purpose releasing air depending on the pressure in the system. Thus, the model or type pressure release valve is in no way limiting.

Notably, the device, in accordance with principles of the present invention is useful with a wide variety of pressure measuring devices or similar devices that achieves the purpose of measuring the pressure in the system. Thus, the model or type pressure measuring devices is in no way limiting.

EXAMPLES

In the examples disclosed below the performance of the invention in simulated neonatal breathing is illustrated.

The additional work needed to breathe through a device can be established by determining imposed work of breathing. This is the additional energy needed for one breath and is closely related to maintaining a stable airway pressure. The imposed work of breathing can be determined in simulated breathing in a mechanical lung model by calculating the area within the pressure-volume loop for one breath.

The method used in the tests is the mechanical lung model which uses a symmetrical sinusoid flow pattern with a flow maximum of 6 liters per minute and a respiratory rate of 60 breaths per minute. The systems and prototypes were all tested at room temperature with piped medical air and a fresh gas flow of 12 liters per minute. Two commercially available T-piece devices were tested, the GE Healthcare T-piece and the Neopuff™ from Fisher & Paykel, and two prototypes A and B representing the present invention. Prototype A used the device described in FIG. 1 and prototype B used the device described in FIG. 3. The parts used for the two prototypes were 1) low resistance connectors between infant interface 5 and positive pressure release valve 6 with the narrowest diameter of >6 mm in prototype A, and 6 mm in prototype B; 2) low resistance connectors between infant interface 5 and open end outlet 8 with a narrowest part of 2×3.5 mm diameter; 3) low restive infant interface 5 with a narrower part of 3×3.5 mm diameter; 4) the pressure release valve 6 used was a Berner valve; 5) the pressure measure device 7 was a standard mechanical pressure meter; 6) double rotameters were used as a shunt 11 to divide the fresh gas flow 10 and adjust the level of CPAP (mean pressure); 7) The variable flow CPAP device 3 was a jet device. 8) Other connectors or tubes had varying flow resistance and diameters.

The results of the imposed work of breathing at different mean pressures for the tested systems are presented in FIG. 7. One mark represents the energy needed for one breath at that mean pressure.

The results in FIG. 7 clearly show the significant reduction in imposed work of breathing for a device according to the present invention illustrated by the two prototypes A and B compared to the tested T-piece devices.

A typical CPAP level for resuscitating or stabilising an infant is in the range of 5-10 cm $H_2O$. A typical peak pressure for PPV is 20-30 cm $H_2O$. It is obtained by occluding the systems, prototypes or T-piece device, respectively and having a correctly adjusted pressure release valve.

Above embodiments of the device and system according to the present invention as defined in the appended claims have been described. These should only be seen as merely non-limiting examples. As understood by the person skilled in the art, many modifications and alternative embodiments are possible within the scope of the invention as defined by the appended claims.

It is to be noted that for the purposes of his application, and in particular with regard to the appended claims, the word "comprising" does not exclude other elements or steps, and the word "a" or "an" does not exclude a plurality, which per se will be evident to a person skilled in the art.

The invention claimed is:

1. A device for positive pressure ventilation and continuous positive airway pressure treatment for neonatal resuscitation comprising:
    a first fresh gas flow tube, configured to provide a first fresh gas flow;
    a variable flow continuous positive airway pressure generator configured to generate a continuous positive airway pressure level, the variable flow continuous positive airway pressure generator comprising first, second and third connection portions, wherein the first fresh gas flow tube is connected with the first connection portion, wherein the generated continuous positive airway pressure level is adjusted by varying the first fresh gas flow to the variable flow continuous positive airway pressure generator;
    a connector connected with the second connection portion of the variable flow continuous positive airway pressure generator, wherein the connector is configured to be connected with an infant interface; and
    a pressure release valve, configured to prevent an excessive positive pressure in a positive pressure ventilation mode;
    wherein the third connection portion comprises an occludable open end defining an outlet, the device further comprising:
        a second fresh gas flow tube, configured to provide a second fresh gas flow, which is added to the first fresh gas flow in the positive pressure ventilation mode,
    wherein the second fresh gas flow tube is connected through a wall of one of the connector and the third connection portion, wherein the pressure release valve is connected through a wall of the second fresh gas flow tube;
    wherein the open end is configured to control a mode of operation of the device based on controlling the second fresh gas flow, such that
        when the open end is non-occluded, the second fresh gas flow flows out of the outlet to configure the device to operate in a continuous positive airway pressure mode, and
        when the open end is occluded, the second fresh gas flow adds to the first fresh gas flow to configure the device to operate in the positive pressure ventilation mode, and
    wherein the device is free from mechanical valves at the outlet.

2. The device according to claim 1, wherein the second fresh gas flow tube is connected with the connector.

3. The device according to claim 1, wherein the second fresh gas flow tube is connected with the third connection portion.

4. The device according to claim 1, where the first fresh gas flow to the variable flow continuous positive airway pressure generator is 3-12 liters per minute and the second fresh gas flow is 3-12 liters per minute.

5. The device according to claim 1, further comprising a pressure measuring device.

6. A system for positive pressure ventilation and continuous positive airway pressure treatment for neonatal resuscitation comprising the device according to claim 1, and a fresh gas connection unit, connected with the first and second fresh gas flow tubes, and connectable to at least one fresh gas source.

7. The system according to claim 6, configured such that when the open end of the open end of the variable flow continuous positive airway pressure generator is occluded, system pressure will increase from the variable continuous positive airway pressure generator until an opening pressure of the pressure release valve is reached, the increase in pressure will result in an inspiratory flow, the system pressure will remain at a set positive pressure ventilation pressure until the occlusion of the open end is removed, and when the open end is non-occluded again the system pressure will return to a set continuous positive airway pressure level and this reduction in pressure will lead to an expiratory flow.

8. The system according to claim 6, configured such that during spontaneous breathing, an infant flow and at least the first fresh gas flow leaves the system over the variable flow continuous positive airway pressure generator, which keeps a positive pressure within an airway stable, and that by varying the first fresh gas flow a continuous positive airway pressure in the airway can be adjusted as needed.

9. A method of treatment for neonatal resuscitation, comprising:
    arranging a device according to claim 1 at an infant; and
    applying positive pressure ventilation and positive airway pressure treatment to the infant through the device.

10. A method of treatment for neonatal resuscitation, comprising:
    arranging the system according to claim 6 at an infant; and
    applying positive pressure ventilation and positive airway pressure treatment to the infant through the device.

11. A device for positive pressure ventilation and continuous positive airway pressure treatment for neonatal resuscitation comprising:
    a continuous flow first fresh gas flow tube, configured to provide a continuous first fresh gas flow;
    a continuous flow second fresh gas flow tube, configured to provide a continuous second fresh gas flow, which is added to the first fresh gas flow in a positive pressure ventilation mode;
    a variable flow continuous positive airway pressure generator configured to generate a continuous positive airway pressure level, the variable flow continuous positive airway pressure generator comprising first, second and third connection portions, wherein the first fresh gas flow tube is connected with the first connection portion, wherein the generated continuous positive airway pressure level is adjusted by varying the first fresh gas flow to the variable flow continuous positive airway pressure generator;
    a connector connected with the second connection portion of the variable flow continuous positive airway pressure generator;
    an infant interface connected with the connector; and
    a pressure release valve, configured to prevent an excessive positive pressure in a positive pressure ventilation mode;
        wherein the third connection portion embodies an outlet of the variable flow continuous positive airway pressure generator, which outlet is tubular and ends with an occludable open end;
        wherein a portion of the first fresh gas tube at the first connection portion being positioned adjacent to and extending at an acute angle to the tubular outlet, and being directed towards the infant interface;

wherein the second fresh gas flow tube is connected through a wall of the third connection portion, between the first connection portion and the open end;
wherein the device is free from mechanical valves between the infant interface and the open end;
wherein the open end is configured to control a mode of operation of the device based on controlling the second fresh gas flow, such that
when the open end is non-occluded, the second fresh gas flow flows out of the outlet to configure the device to operate in a continuous positive airway pressure mode, and
when the open end is occluded, the second fresh gas flow adds to the first fresh gas flow to configure the device to operate in the positive pressure ventilation mode.

12. A method of providing positive pressure ventilation and continuous positive airway pressure treatment for neonatal resuscitation comprising:
performing the method using a device comprising a variable flow continuous positive airway pressure generator, which is configured to generate a continuous positive airway pressure level and which includes first, second and third connection portions, and a connector connected with the second connection portion, wherein the connector is configured to be connected with an infant interface, wherein the third connection portion comprises an occludable open end defining an outlet, and wherein the device is free from mechanical valves between the infant interface and the open end;
providing a continuous first fresh gas flow to the first connection;
adjusting the generated continuous positive airway pressure level by varying the first fresh gas flow to the variable flow continuous positive airway pressure generator;
providing a continuous second fresh gas flow to one of the connector and the third connection portion;
controlling a mode of operation of the device by operating the open end, comprising occluding the open end to configure the device to operate in a positive pressure ventilation mode, wherein the second fresh gas flow adds to the first fresh gas flow, and non-occluding the open end to configure the device to operate in a continuous positive airway pressure mode, wherein the second fresh gas flow flows out of the outlet.

* * * * *